United States Patent [19]

Heitz et al.

[11] Patent Number: 4,758,652

[45] Date of Patent: Jul. 19, 1988

[54] PROCESS FOR PREPARING OLIGOMERS AND TELECHELS HAVING CARBOXY-PIPERAZINE UNITS, AND NEW OLIGOMERS AND TELECHELS OF POLY(CARBOXYPIPERAZINE)

[75] Inventors: Walter Heitz, Kirchhain; Reinhold Schwalm, Wachenheim, both of Fed. Rep. of Germany

[73] Assignee: Bayer AG, Leverkusen, Fed. Rep. of Germany

[21] Appl. No.: 931,353

[22] Filed: Nov. 17, 1986

[30] Foreign Application Priority Data

Nov. 29, 1985 [DE] Fed. Rep. of Germany ....... 3542230

[51] Int. Cl.[4] .................. C08G 63/62; C09K 3/00; C07D 241/04
[52] U.S. Cl. ........................... 528/369; 528/372; 544/387; 544/360; 544/357; 252/182.28
[58] Field of Search ............... 544/387, 360, 357; 528/369, 372; 252/182

[56] References Cited

U.S. PATENT DOCUMENTS 2,717,896  9/1955  Goldman .................. 544/388
3,130,179  4/1964  Cotter ..................... 528/368
3,954,770  5/1976  Mayerhoefer et al. ....... 544/388
4,165,424  8/1979  Hermans .................. 528/72

FOREIGN PATENT DOCUMENTS 772147  4/1957  United Kingdom .

OTHER PUBLICATIONS

Chemical Abstracts, vol. 82, Nr. 17, Apr. 28, 1975, Columbus, Ohio, M. I. Doroklova, "Synthesis of 1-methyl-piperazine", p. 511 (112033n).
Australian Journal of Chemistry, vol. 19, 1966, Melbourne, D. E. Rivett et al., "Some Reactions of 1,4-Bischlorocarbonylpiperazine", pp. 869–875.
Die Makromolekulare Chemie, Bol. 187, Nr. 6, Jun. 1986.
R. Schwalm et al., "Syntheses of Telechelic Oligo-and poly(carboxypiperazine)s", pp. 1415–1422.

Primary Examiner—Harold D. Anderson
Assistant Examiner—Dennis R. Daley
Attorney, Agent, or Firm—Connolly & Hutz

[57] ABSTRACT

A process for preparing oligomers and telechels of poly(carboxy-piperazine) and new oligomers the telechels of poly(carboxy-piperazine), wherein the process involves condensation of piperazine or piperazine-N-carboxylic acid esters or their reaction with piperazine or piperidine derivatives to form an intermediate which is reacted with diphenyl carbonate in the presence of a tertiary amine.

6 Claims, No Drawings

PROCESS FOR PREPARING OLIGOMERS AND TELECHELS HAVING CARBOXY-PIPERAZINE UNITS, AND NEW OLIGOMERS AND TELECHELS OF POLY(CARBOXYPIPERAZINE)

The invention relates to a process for preparing oligomers and telechels of poly(carboxy-piperazine) and to new oligomers and telechels of poly(carboxy-piperazine).

High-melting, polymeric poly(carboxy-piperazine) and its preparation is known for example from U.S. Pat. No. 3,130,179. Aust. J. Chem. 19, 869 (1966) for example, discloses reacting N,N'-di(chlorocarbonyl)piperazine with a number of compounds, inter alia phenol, piperidine, N-carboxyethylpiperazine. The reaction product with N-carboxyethylpiperazine forms on hydrolysis also the trimer

A process has been found for preparing oligomers and telechels of poly(carboxy-piperazine), as well as new oligomers and telechels of poly(carboxypiperazine) which can be melted without decomposing.

The invention therefore provides a process for preparing oligomeric and telechelic poly(carboxy-piperazines) of the formula (I)

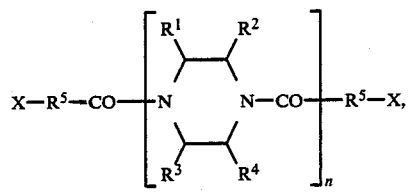

in which
R$^1$, R$^2$, R$^3$ and R$^4$ independently of one another stand for hydrogen, C$_1$-C$_6$-alkyl, C$_5$-C$_8$-cycloalkyl, C$_6$-C$_{10}$-cycloalkylalkyl, C$_6$-C$_{10}$-aryl and C$_7$-C$_{14}$-aralkyl,
R$^5$ stands for

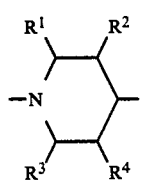

wherein R$^1$-R$^4$ has the meaning indicated in the case of the formula (I),
and for

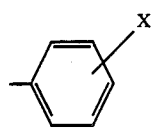

wherein

X stands for hydrogen and has the meaning of one of the radicals R$^1$, R$^2$, R$^3$ or R$^4$,
n stands for the number 1, 2 or 3, those compounds of the formula (I) in which n stands for the number 2 or 3 being new,
characterized in that piperazine or piperazine-N-carboxylic acid esters of the formula (II)

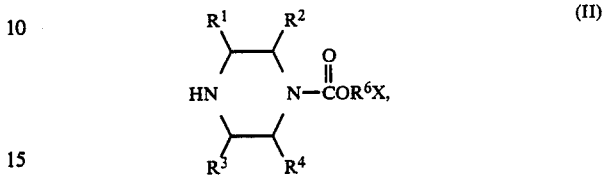

in which
R$^1$ to R$^4$ have the meaning indicated in the case of the formula (I),
R$^6$ stands for C$_1$-C$_{10}$ alkyl, C$_5$-C$_{10}$ cycloalkyl, C$_7$-C$_{17}$ aralkyl, and
X stands for hydrogen and has the meaning of one of the radicals R$^1$, R$^2$, R$^3$ or R$^4$,
are reacted in the presence of tertiary amines with carbonic acid esters of the formula (III)

in which
R$^7$ denotes Cl, —OR$^8$—X,
R$^8$ denotes C$_6$-C$_{14}$ aryl, C$_7$-C$_{20}$ aralkyl and
X stands for hydrogen and has the meaning of one of the radicals R$^1$, R$^2$, R$^3$ or R$^4$,
in aprotic solvents at temperatures of 0° to 200° C. to give N,N'-disubstituted piperazine derivatives of the formula (IV)

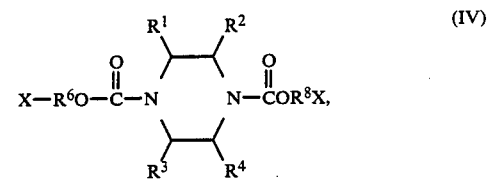

in which
X stands for hydrogen and has the meaning of one of the radicals R$^1$, R$^2$, R$^3$ or R$^4$,
R$^6$ has the meaning indicated in the case of formula (II) or for R$^8$,
R$^8$ has the meaning indicated in the case of formula (III),
and subsequently the active ester group

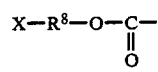

is reacted with piperazine or piperidine derivatives, or the unreacted group

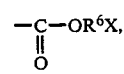

wherein $R^6$ and X have the meaning indicated in the case of the formula (I) and (II), is split off at temperatures of 0° to 100° C. with aqueous alkaline earth metal solution, and the resulting piperazine derivative of the formula (V)

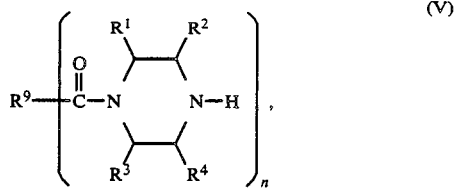

in which
n, $R^1$ or $R^4$ have the meaning indicated in the case of formula (I) and
$R^9$ stands for $R^5$ (n=1), or for

(n=2), is reacted with diphenyl carbonate at temperatures of 100° to 250° C. in the presence of tertiary amines.

The compounds of the formula V with

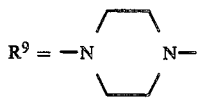

can similarly be reacted with acid chlorides

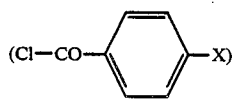

to give telechels, or the reaction products with diphenyl carbonate can likewise be further reacted with piperidine derivatives

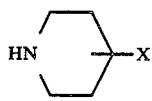

in the presence of tertiary amines to give oligomers (X=H) or telechels.

The compounds according to the invention are meltable without decomposing. They do not decompose until above 360° C. From the melting points of the oligomers, the melting point of poly(carboxypiperazine) can be extrapolated to about 800° C. and hence can be above the decomposition temperature.

The oligomers and telechels of carboxypiperazine, as polyureas of secondary diamines, have a remarkable hydrolysis stability and, since they have a high crystallinity, can preferably be incorporated as blocks in organic synthetic fibre and film materials such as polyamides and polyurethanes, and also in construction thermoplastics such as aliphatic polyamides, polyphenylene sulphides and the like.

Preferred oligomers and telechels of the formula (I) are those in which $R^1$ to $R^4$ can be monovalent $C_1$-$C_6$-alkyl radicals, hydrogen, $R^5$ can be —OR—,

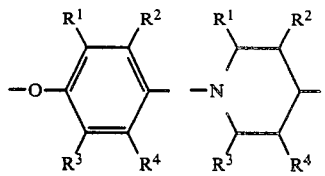

and X can be=H—, —COOR (R=$C_1$-$C_4$-alkyl), —COOH, —COCl, —CH$_2$OH, halogen such as Cl, Br, CN and the like.

Preferred monovalent hydrocarbon radicals $R^1$, $R^2$, $R^3$, $R^4$ are for example alkyl radicals such as methyl, ethyl, n-propyl, n-butyl, isobutyl; preferred cycloalkyl radicals are for example cyclohexyl, cyclopentyl; preferred cycloalkylalkyl radicals are for example alkyl radicals having cycloalkyl substituents, for example cyclohexamethyl, preferred aromatic hydrocarbons is for example phenyl.

It is preferably possible to use piperazines with $R^1$, $R^2$, $R^3$, $R^4$, which can be identical or different, such as hydrogen or monovalent hydrocarbons having 1 to 6 carbon atoms.

Examples of particularly preferred piperazines to be used according to the invention are 2-methylpiperazine, 2,5-dimethylpiperazine, 2-isobutylpiperazine, 2-cyclohexylpiperazine, 2-phenylpiperazine.

The radicals $R^5$ are those such as alkoxy radicals which are derived from the meanings of the radicals $R^1$, $R^2$, $R^3$, $R^4$, for example $C_6$-$C_{10}$-aryloxy such as phenylene and phenyleneoxy radicals, piperidine radicals with $R_1$ equal to the previously defined meaning. Suitable groups X are hydrogen, —COOR with R equal to the previously defined meaning for $R^1$ to $R^4$, —COOH, —$R^6$—OH with $R^6$=$C_1$-$C_8$-alkylene, —COCl; halogen such as Cl, Br, —CN.

To introduce the —$R^5$—X radicals it is possible to use for example:

piperidine, 4-piperidinecarboxylic acid, ethyl 4-piperidinecarboxylate, 2-piperidinemethanol, 2-piperidineethanol, 3-piperidinemethanol, p-chlorophenyl, m-chlorophenyl, o-chlorophenyl, p-bromophenyl, phenoxy, p-chlorophenoxy radicals.

The preparation of the oligomers and telechels of the formula I with n=2 can be represented by means of the following diagram:

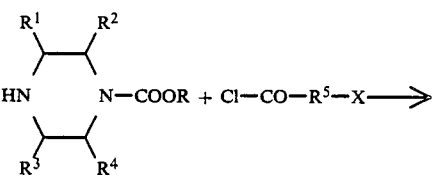

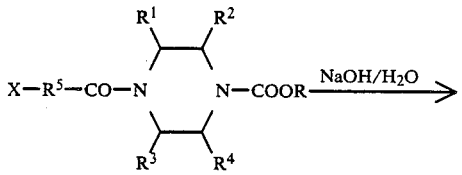

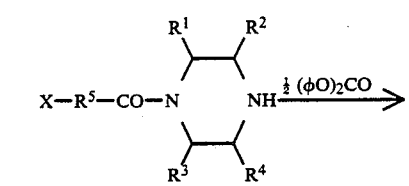
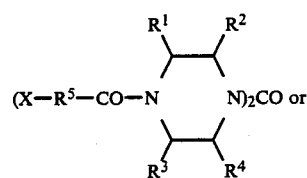
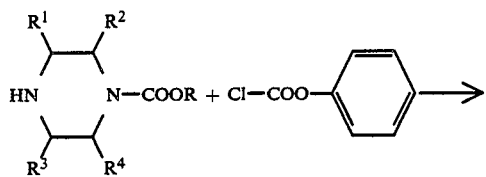
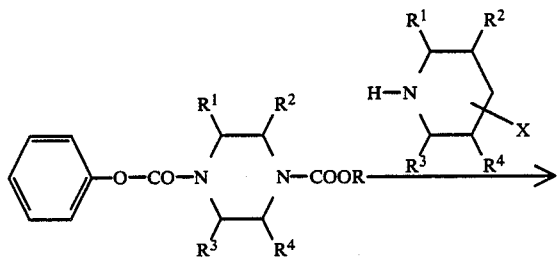
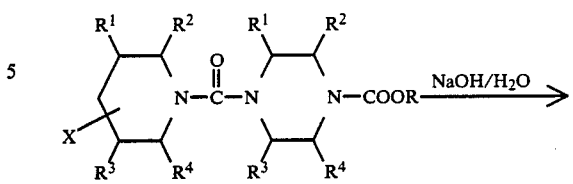
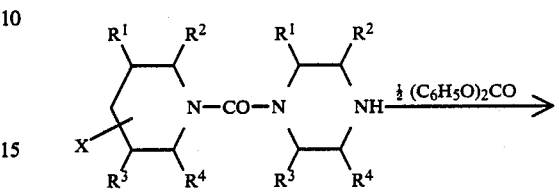
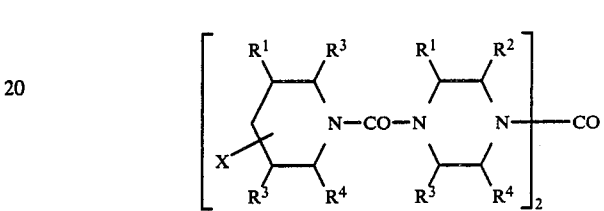
where
  the radicals $R^1$, $R^2$, $R^3$, $R^4$, $R^5$, R, X have the meaning indicated in the case of the formula (I).
The oligomers and telechels of the formula (I) with $n=3$ can be prepared in accordance with the following reaction diagram:
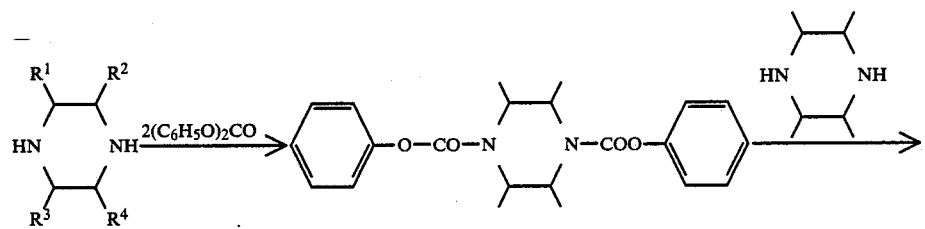
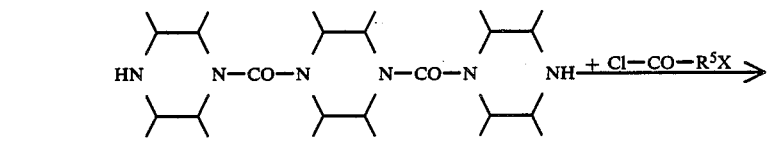
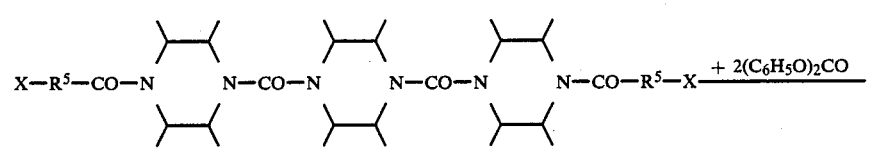
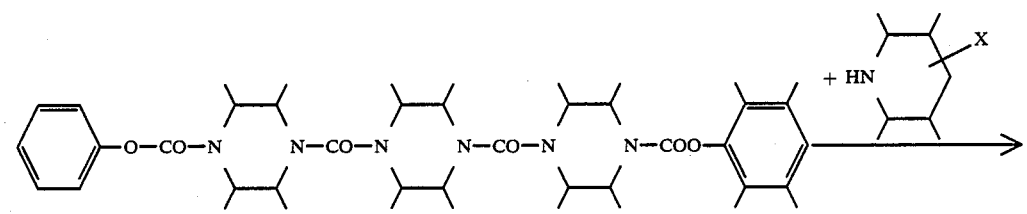

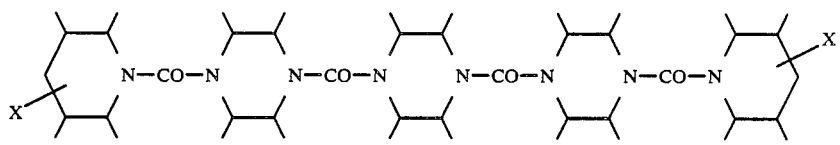

The telechels prepared according to the invention can be further reacted via their reactive end groups, and they can be used for building up other plastics.

The oligomers and telechels of poly(carboxypiperazine) which are preparable according to the invention can be melted without decomposing, unlike the polymer, and therefore can also be used for building up polycondensates. They are incorporated in suitable form, for example with carboxyphenyl end groups, in aliphatic and aromatic polyesters and polycarbonates, in polyamides and polyurethanes. In these polymers they form rigid segments, increase the crystallinity, the stiffness and hardness and contribute to the flameproofing of these polycondensates.

To prepare the oligomers or telechels, the compounds of the formula IV were reacted in the presence of tertiary amines with piperazine or piperidine derivatives, so that all active aromatic ester groups are converted to ureas. If the compound of the formula IV is asymmetrically substituted, the remaining alkyl ester group is split off at 0° to 100° C. using aqueous alkali metal hydroxide solution (concentration 2.1-10N). The resulting compounds of the formula V are then further reacted, via the secondary amine group, to give the oligomers or telechels. The reaction of optionally substituted compounds of the formula V can be effected at temperatures of 0° to 300° C. with acid chlorides in the presence of tertiary amines or with diphenyl carbonate in the molar ratio of 1:2 to 2:1.

This reaction can be carried out in the absence or presence of solvents. Examples of solvents which can be used are: alcohols, phenols, halogenohydrocarbons, aromatic hydrocarbons, ethers. The tertiary amines used can be aromatic amines such as pyridine, aliphatic amines such as triethylamine and the like.

EXAMPLE 1

Preparation of poly(carbox-piperazine) with piperidine end group with n=2 (in accordance with the formula I)

A 250 ml three-necked flask with reflux condenser, $N_2$ inlet tube and dropping funnel is charged with 25 g (150 mmol) of ethyl piperazine-N-carboxylate, 30 ml of pyridine and 50 ml of dry chloroform, and 24.6 g (158 mmol) of phenyl chloroformate in 50 ml of chloroform are gradually added dropwise at room temperature; this is followed by refluxing for 1 h. Chloroform is distilled off, the residue is added to ice-water, which is followed by acidification with dilute hydrochloric acid, and the reaction product is extracted with ether. Removal of the ether by distillation leaves behind 38.6 g of ethyl phenyl piperazine-N,N-dicarboxylate (IR: 1723 $cm^{-1}$ >N—CO—O$\phi$; 1698 $cm^{-1}$ >N—COOEt).

14.4 g (52 mmol) of ethyl phenyl piperazine-N,N'-dicarboxylate are heated together with an excess of piperidine (10 g=118 mmol) to the boil in a 100 ml two-necked flask with reflux condenser and internal thermometer. The internal temperature rises in the course of 12 h from 130° C. to 175° C. The reaction is monitored by means of IR spectroscopy (>N—CO—O$\phi$ 1723 $cm^{-1}$ disappears and a new urea band N—CO—N forms at 1640 $cm^{-1}$. Yield: 9.0 g (64%).

The product was subsequently hydrolized. To this end, the 9.0 g of the N-ethoxycarbonyl derivative obtained were refluxed for five hours in 250 ml of ethanol together with 200 ml of 10% NaOH.

Ethanol is distilled off, and the solution is saturated with sodium chloride and extracted with chloroform. After drying with $Na_2SO_4$ the chloroform is distilled off. This gives 3.1 g (=48% yield) of the N-carboxypiperidinepiperazine.

3.0 g (15 mmol) of piperazine-N-carboxypiperidine are heated together with 1.5 g (7 mmol) of diphenyl carbonate and 2.0 g of 4-dimethylaminopyridine as a base to 210° C. in the melt for 5 h. After cooling down, the reaction mixture is stirred into 10% NaOH, and the precipitated solid is filtered off with suction. The IR spectrum of this solid shows in addition to the absorption band at 1640 $cm^{-1}$ also a weak band at 1720 $cm^{-1}$ (>N—COO$\phi$) which comes from the monosubstitution product with diphenyl carbonate. By repeatedly extracting with acetone the byproduct is removed and the reaction product is recrystallized twice from $CH_2Cl_2$/hexane. 0.96 g (=33% of theory) of the oligomer is obtained.

Melting point: 267° C.

|  | C | H | N | O |
|---|---|---|---|---|
| calc. | 59.97 | 8.63 | 19.98 | 11.41 |
| fnd. | 60.12 | 8.35 | 20.00 | 12.03 |

Infrared absorption band ($cm^{-1}$):
1639 (C=O stretching vibration for ureas). Mass spectrum: M+: 420 (45% at 28 eV).

EXAMPLE 2

Preparation of poly(carboxy-piperazine) with phenyl carboxylate end groups (n=3, in accordance with the formula I)

43.0 g (0.5 mmol) of piperazine are refluxed for 20 hours with 214 g (1 mol) of diphenyl carbonate and 300 ml of methanol. Cooling down is followed by filtration with suction and recrystallization from ethanol. The resulting piperazine diphenyl ester has a melting point of 181° C.

In an apparatus comprising a 500 ml three-necked flask, reflux condenser, thermometer and solids-metering funnel, 20 g (61 mmol) of the piperazine diphenyl ester are added by means of the solids-metering funnel at 150° C. to a 10-fold excess (52 g) of piperazine in the course of 8 hours. The reaction mixture is allowed to cool down and is stirred with dilute NaOH overnight. The solution is saturated with sodium chloride and extracted with chloroform. After drying with $Na_2SO_4$ chloroform is distilled off and the piperazine likewise extracted in small amounts is removed by distillation. The reaction product, 1,4-bis-(piperazino-carbonyl- )piperazine, is recrystallized from CH$_2$Cl$_2$/hexane. Melting point 211° C.

2.0 g (6.5 mmol) of 1,4-bis-(piperazinocarbonyl)piperazine are refluxed for 20 hours in a 100 ml three-necked flask with reflux condenser and a thermometer with 3.0 g (14 mmol) of diphenyl carbonate in 20 ml of ethanol. The precipitated solid is recrystallized from aqueous acetone. Yield: 2.61 g (=75% of theory).

Melting point: 248° C.

|       | C     | H    | N     | O     |
|-------|-------|------|-------|-------|
| calc. | 61.07 | 6.22 | 15.26 | 17.43 |
| fnd.  | 611.4 | 6.32 | 15.36 | 17.06 |

Infrared absorption band (cm$^{-1}$):
1639 (C=O stretching vibration for >N—CO—N<)
1723 (C=O stretching vibration for >N—CO—O<).

EXAMPLE 3

Preparation of poly(carboxy-piperazine) with piperidine end groups (n=3, in accordance with the formula I)

1.0 g (1.8 mmol) of the diphenyl ether of 1,4-bis(-piperazinocarbonyl)-piperazine prepared in Example 2 is heated to 250° C. for 2 hours in a 50 ml glass autoclave together with 2.0 g (23.5 mmol) of piperidine. In the course of the heating the pressure rises to 6 bar. The reaction product is stirred overnight in dilute NaOH, and the precipitated solid is filtered off with suction and is recrystallized twice from CH$_2$Cl$_2$/hexane.

Melting point: 334° C.

|       | C     | H    | N     | O     |
|-------|-------|------|-------|-------|
| calc. | 58.62 | 8.32 | 21.03 | 12.01 |
| fnd.  | 58.97 | 8.34 | 21.05 | 12.09 |

Infrared absorption band (cm$^{-1}$):
1639 (C=O stretching vibration for >N—CO—N<).
Mass spectrum M+ at m/e 532 (100% at 28 eV).

EXAMPLE 4

. . . prepare poly(carboxy-piperazine) with p-chlorophenyl end groups, 4.65 g (15 mmol) of the 1,4-bis-(piperazinocarbonyl-)piperazine prepared in Example 2 are reacted with 6.2 g (36 mmol) of p-chlorobenzoyl chloride. The acid chloride is presented together with 3.0 g of pyridine (39 mmol) and 60 ml of dry CH$_2$Cl$_2$, and the amine, dissolved in 40 ml of CH$_2$Cl$_2$, is added dropwise in the course of an hour. This is followed by a further hour of refluxing and stirring . . . at room temperature. The reaction mixture is discharged into methanol, and the precipitated product is filtered off with suction, washed with NaHCO$_3$ solution, water and methanol and dried at 60° C. in a drying cabinet. Yield: 6.38 g (=72.5%). This is followed by recrystallization from N-methylpyrrolidone.

Melting point: 313° C.

|       | C     | H    | N    | Cl    |
|-------|-------|------|------|-------|
| calc. | 57.23 | 5.49 | 14.3 | 12.06 |
| fnd.  | 57.22 | 5.57 | 14.28| 11.98 |

Mass spectrum M+ 586 (87%), 588 (50%), 590 (12%).

We claim:

1. Process for preparing an oligomeric poly(carboxypiperazine) compound of the formula (I)

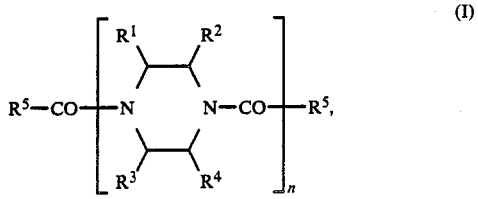

in which
R$^1$, R$^2$, R$^3$, and R$^4$ independently of one another stand for hydrogen, C$_1$–C$_6$-alkyl, C$_5$–C$_8$-cycloalkyl, C$_6$–C$_{10}$-cycloalkylalkyl, C$_6$–C$_{10}$-aryl and C$_7$–C$_{14}$-aralkyl,
R$^5$ stands for

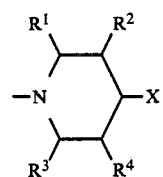

wherein R$^1$–R$^4$ has the meaning indicated in formula (I), and for

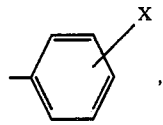

wherein
X stands for hydrogen, —COOH, —COO(C$_1$–C$_4$-alkyl), —COCl, —CH$_2$OH, —CN or halogen, and n stands for the number 1, 2 or 3,
characterized in that piperazine or piperazine-N-carboxylic acid esters of the formula (II)

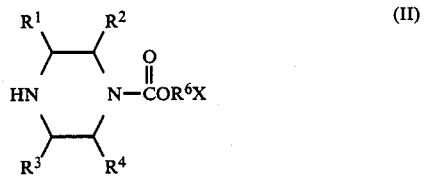

in which R$^1$ to R$^4$ have the meaning indicated in formula (I),
R$^6$ stands for C$_1$–C$_{10}$ alkyl, C$_5$–C$_{10}$ cycloalkyl, C$_7$–C$_{17}$ aralkyl,
X stands for hydrogen, —COOH, —COO(C$_1$–C$_4$ alkyl), —COCl, —CH$_2$OH, or halogen,
are reacted in the presence of tertiary amines with carbonic acid esters of the formula (III)

$$R^7-\overset{O}{\underset{\|}{C}}-OR^8-X \quad (III)$$

in which
- $R^7$ denotes Cl, $-OR^8-X$,
- $R^8$ denotes $C_6-C_{14}$ aryl, $C_7-C_{20}$ aralkyl and
- X has the meaning indicated in formula (II), in an aprotic solvent which is an alcohol, a phenol, a halohydrocarbon, an aromatic hydrocarbon or an ether at temperatures of 0° to 200° C. to give N,N'-disubstituted piperazine derivatives of the formula (IV)

$$X-R^6O-\overset{O}{\underset{\|}{C}}-N\underset{R^3\ R^4}{\overset{R^1\ R^2}{\diagup\diagdown}}N-\overset{O}{\underset{\|}{C}}OR^8X \quad (IV)$$

in which
- X has the meaning indicated in formula (II),
- $R^6$ has the meaning indicated in formula (II) or for $R^8$,
- $R^8$ has the meaning indicated in formula (III), and subsequently the active ester group $$X-R^8-O-\overset{}{\underset{\|}{C}}-\\ \phantom{X-R^8-O-}O$$

is reacted with piperazine or piperidine derivatives, or the unreacted group $$-\overset{}{\underset{\|}{C}}-OR^6X,\\ O$$

wherein $R^6$ and X have the meaning indicated in formula (II), is split off at temperatures of 0° to 100° C. with aqueous alkaline (earth) metal solution, and the resulting piperazine derivatives of the formula (V)

$$\left\{R^9\left|\underset{R^3\ R^4}{\overset{R^1\ R^2}{-\overset{O}{\underset{\|}{C}}-N\diagup\diagdown N-H}}\right.\right\}_n \quad (V)$$

in which
- n, $R^1$ to $R^4$ have the meaning indicated in formula (I) and
- $R^9$ stands for $R^5$ where n is 1, or for $$-N\diagup\diagdown N-$$

where n is 2, is reacted with diphenyl carbonate at temperatures of 100° to 250° C. in the presence of tertiary amines.

2. The process according to claim 1 wherein the tertiary amine is pyridine or triethylamine.

3. Oligomeric and telechelic poly(carboxy-piperazine) compound of the formula (I)

$$\left[R^5-CO-N\underset{R^3\ R^4}{\overset{R^1\ R^2}{\diagup\diagdown}}N-CO-R^5\right]_n \quad (I)$$

in which
- $R^1$, $R^2$, $R^3$ and $R^4$ independently of one another stand for hydrogen, $C_1-C_6$-alkyl, $C_5-C_8$-cycloalkyl, $C_6-C_{10}$-cycloalkylalkyl, $C_6-C_{10}$-aryl and $C_7-C_{14}$-aralkyl,
- $R^5$ stands for $$-N\underset{R^3\ R^4}{\overset{R^1\ R^2}{\diagup\diagdown}}X$$

wherein $R^1-R^4$ has the meaning indicated in formula (I), and for (phenyl ring with X substituent), wherein
- X stands for hydrogen —COOH, —COO ($C_1-C_4$ alkyl), —COCl, —CH$_2$OH, CN, halogen, and
- n stands for the number 2 or 3.

4. A compound of the formula (I) according to claim 3 wherein n is 2.

5. A compound of the formula (I) according to claim 3 wherein n is 3.

6. A mixture of two compounds of the formula (I) according to claim 3 wherein for one compound n is 2 and for the other compound n is 3.

* * * * *